Figure 1:
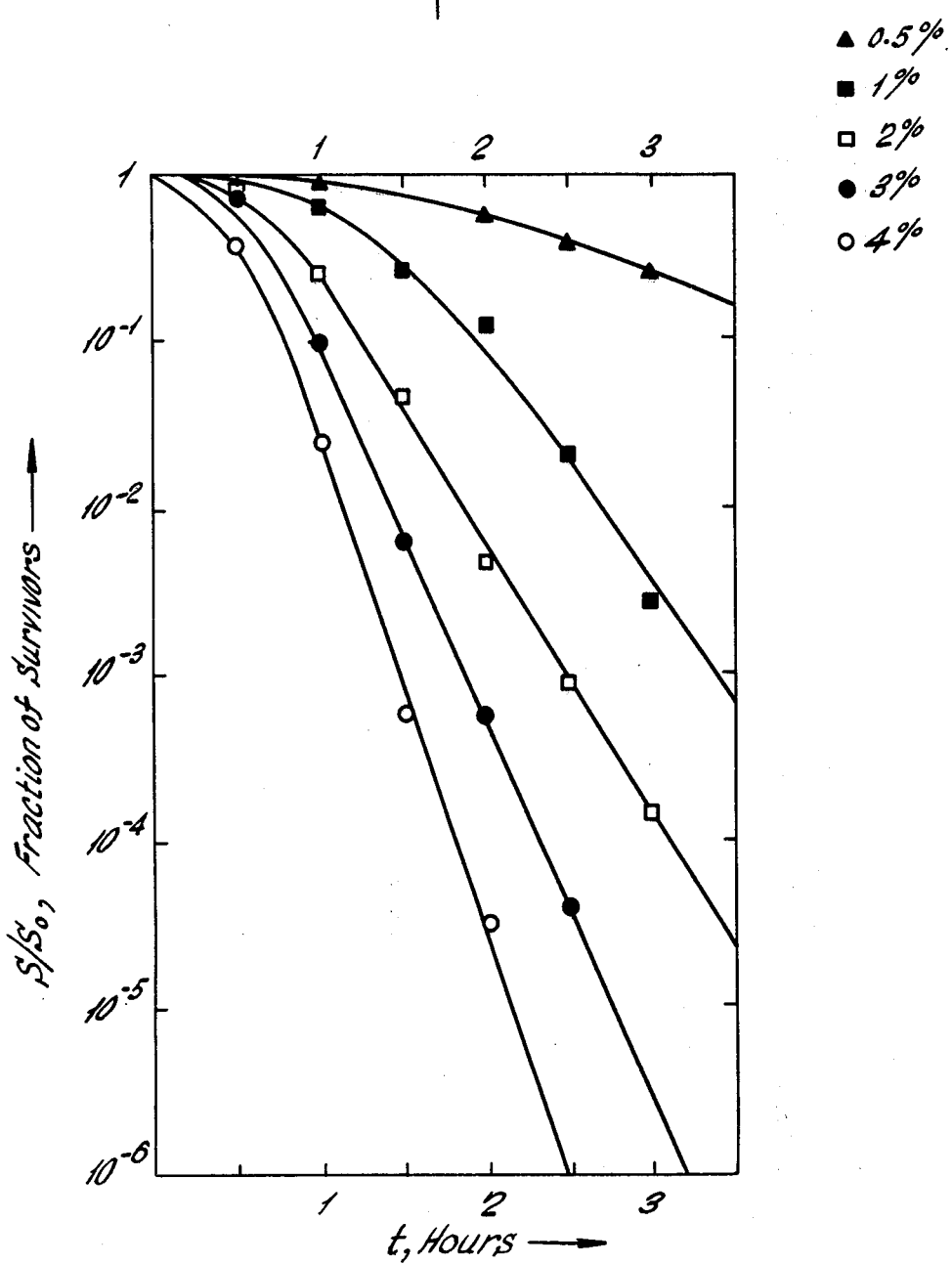

United States Patent [19] [11] 4,173,653
Law [45] Nov. 6, 1979

[54] OXYDIACETALDEHYDE COMPOSITIONS USED AS DISINFECTANTS

[75] Inventor: David C. F. Law, Arlington, Tex.

[73] Assignee: Arbrook, Inc., Arlington, Tex.

[21] Appl. No.: 531,842

[22] Filed: Dec. 11, 1974

[51] Int. Cl.² ............................................. A01N 9/24
[52] U.S. Cl. ................................................. 424/333
[58] Field of Search ...................................... 424/333

[56] References Cited

U.S. PATENT DOCUMENTS

| | | | |
|---|---|---|---|
| 3,304,179 | 2/1967 | Field et al. | 96/61 |
| 3,697,222 | 10/1972 | Sierra | 424/333 |

*Primary Examiner*—Leonard Schenkman

[57] ABSTRACT

Oxydiacetaldehyde is an active antimicrobial agent when used in aqueous solution for disinfecting or sterilizing purposes. The activity of such solutions against bacteria or spores can be improved by adding alkalinating agents, e.g., sodium acetate, or alcohols, e.g., isopropanol or propylene glycol, or by raising pH or temperature.

9 Claims, 1 Drawing Figure

OXYDIACETALDEHYDE COMPOSITIONS USED AS DISINFECTANTS

FIELD OF THE INVENTION

This invention relates to improved chemical sterilization and disinfecting solution compositions, more particularly to compositions utilizing oxydiacetaldehyde as the active antimicrobial agent, and to methods for disinfecting with such compositions.

Chemical disinfection of medical and surgical materials is becoming increasingly important, and glutaraldehyde has proved to be one of the more important instrument-equipment germicides as a 2 percent alcoholic solution, or especially as a 2 percent aqueous solution alkalinized to pH 7.5 or above. Patents referring to the use of glutaraldehyde for such purposes include:

PRIOR ART (a) Pepper et al. U.S. Pat. No. 3,016,328, which teaches disinfecting with a sporicidal composition containing a $C_{2-6}$ saturated dialdehyde, such as glutaraldehyde, and an alkalinating agent in either alcoholic solution, or in aqueous solution at above pH 7.4.

(b) Stonehill U.S. Pat. No. 3,282,775, which teaches disinfecting with sporicidal compositions containing a saturated $C_{2-6}$ dialdehyde, preferably glutaraldehyde, and a cationic surface active agent.

(c) Sierra U.S. Pat. No. 3,697,222, which teaches both sterilizing by contacting the material to be treated with an aqueous acid glutaraldehyde solution at temperatures above 45° C. and also by simultaneously subjecting the above solution to sound energy.

(d) Boucher U.S. Pat. No. 3,708,263, which teaches sterilizing at low temperatures by contacting the material to be treated with a chemical solution comprising an aqueous glutaraldehyde (at pH 2–8.5) and dimethylsulfoxide and ultrasonic waves simultaneously at temperatures below 75° C.

(e) Winicov et al. (West Laboratories) South African published patent application No. 72/4044, which teaches sporicidal compositions containing glutaraldehyde at pH 6.5–7.4, which may contain a detergent and also may contain a monoaldehyde.

SUMMARY OF THE INVENTION

It has now been discovered that improved or similar results are obtained when the glutaraldehyde used in the compositions and processes of the aforementioned patents is replaced by oxydiacetaldehyde. These oxydiacetaldehyde compositions are used in the same way and with the same modes of application as the prior art glutaraldehyde compositions. At equal concentrations oxydiacetaldehyde is slightly less active than glutaraldehyde.

It has also been discovered that oxydiacetaldehyde is an active antimicrobial agent, in solutions, which is capable of disinfecting medical and surgical instruments and household objects and the like which are treated with compositions containing oxydiacetaldehyde, and that such oxydiacetaldehyde solutions can even sterilize contaminated objects contacted with such solutions so that any spores which may be present are destroyed. It has further been discovered that the degree of antimicrobial activity present (i.e., whether the oxydiacetaldehyde solution will be only bactericidal and bacteristatic, or will also be sporicidal) can be enhanced by the addition of other ingredients to the oxydiacetaldehyde containing solution or by the conditions of use.

Oxydiacetaldehyde, which is also called 3-oxaglutaraldehyde or diglycolaldehyde, has the formula $OHCCH_2OCH_2CHO$. It differs from glutaraldehyde, which has the formula $OHCCH_2CH_2CH_2CHO$, in having an oxygen present in the chain instead of a methylene group. Oxydiacetaldehyde has been known since 1961 [see. C. L. Zirkle et al. *J. Org. Chem.*, 26, 395 (1961)]. It has been used mainly as an intermediate in various literature references, and its use also has been taught as a photographic hardening agent for gelatin coatings in Field et al. U.S. Pat. No. 3,304,179. However, the application of oxydiacetaldehyde for disinfection or sterilization has never been known prior to this invention.

Oxydiacetaldehyde appears to be unique in that it is the only member of the oxygen-interrupted-saturated di-aldehyde family to which it belongs which appears to have any appreciable antimicrobial activity. Four homologs of oxydiacetaldehyde were prepared and tested, namely compounds of the formulae $OHCCH_2OCH_2CH_2CHO$, $OHCCH_2O(CH_2CH_2O)_nCH_2CHO$, where n=1 and also where n=2; and

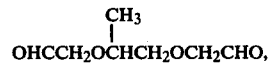

but they were all found to be inactive against bacterial spores or vegetative bacteria.

An aqueous solution of oxydiacetaldehyde is the simplest and most basic antimicrobial composition of this invention. Oxydiacetaldehyde in pure form has a neutral pH. Some processes of manufacture of this compound introduce an acid, e.g., acetic acid, which then lowers the pH because of the presence of small amounts of acid with the oxydiacetaldehyde. However, the compound can be obtained in pure form, or the pH can be adjusted by conventional means to whatever level is desired. The oxydiacetaldehyde solutions of this invention have antimicrobial activity at all pH ranges, (even as low as pH 2.5 which is below the range considered practical or desirable for disinfecting or sterilizing purposes). The pH of these solutions can easily be raised or lowered where desired. Also, the above basic composition may be modified in various ways to meet different requirements of application, as will be described later on, by merely mixing in any additional desired materials.

FIG. 1 in the appended drawing is a graph comparing the activities of oxydiacetaldehyde solutions of varying concentrations against *Bacillus subtilis* ATCC 19659 spores according to the Spore Rate of Kill Test. The solutions tested contained 0.5%, 1%, 2%, 3% and 4% of oxydiacetaldehyde respectively, and all solutions also contained 1.4% sodium acetate and 1% sodium phosphate buffer at pH 8. The graph shows the activity increases with the concentration. One of the compositions shown therein, which is a currently preferred composition consisting of an aqueous solution of 3% oxydiacetaldehyde, 1.4% sodium acetate and 1% disodium phosphate at pH 8 exhibits an activity against *Bacillus subtilis* spores which is equal to that of the well known CIDEX ® Activated Dialdehyde Solution (containing 2.2% glutaraldehyde in aqueous solution with a pH of about 9).

The bactericidal activity of the compositions of this invention is affected primarily by such factors as the oxydiacetaldehyde concentration, pH, temperature, and the presence of synergists, e.g., sodium acetate and/or isopropanol. The activity may also be affected to lesser extents by the ionic strength and surface tension (the latter being affected by the presence of surfactants). Tables 1–8 are presented later on to illustrate these points. Any other desirable ingredients found in currently available disinfecting or sterilizing compositions also may be added provided they are compatible with oxydiacetaldehyde and with each other.

More Detailed Description

The various ingredients which can be used in the compositions of this invention, and the composition-activity relationship under the influence of pH and temperature are as follows:

1. Oxydiacetaldehyde (ODAA): This compound is the active antimicrobial ingredient. Other factors being equal, the antimicrobial activity of the compositions of the present invention increases with increasing proportions of oxydiacetaldehyde. This can especially be seen in Tables 2 and 3 and FIG. 1.

2. Solvent: The preferred solvent used in the disinfecting or sterilizing solutions of the present invention is water, which is nontoxic, inexpensive and commonly used for cleaning purposes. Oxydiacetaldehyde is completely soluble in water at all concentrations. Organic solvents may be added as cosolvents. Among the latter are (a) the lower-alkanols containing 1 to 4 carbons (e.g., methanol, ethanol, the propanols, and the butanols), (b) the glycols containing 2 to 6 carbons (e.g., ethylene glycol, propylene glycol, 2-butene-1, 4-diol, 2-butyne-1,4-diol and 2-methyl-2,4-pentanediol), (c) glycerol and other triols, (d) dimethylsulfoxide, (e) polyethylene glycols.

3. Synergism between alcohols and oxydiacetaldehyde: Although none of the alcohols tested are active by themselves against bacterial spores at the concentrations used (10% to 70%), the addition of certain alcohols (e.g., isopropanol and propylene glycol) to oxydiacetaldehyde solutions has a synergistic effect on the sporicidal activity. The synergistic effect increases with increasing concentrations of the alcohol, as is shown in Table 4.

Some increase in the activity against vegetative bacteria was also observed when isopropanol or propylene glycol was added to the oxydiacetaldehyde solution (e.g., at the 10% alcohol level). However, other alcohols (such as ethanol and hexylene glycol) offer little or no benefit (see Table 4) and have no synergistic effect.

4. Compatible alkalinating agents: A variety of alkalinating agents (compounds that can be used to raise the pH) may be used singly or in combination, which may be inorganic or organic in nature. Examples of usable inorganic alkalinating agents include the alkali metal salts (preferably sodium or potassium) derived from the inorganic acids, such as borates (meta or tetra), carbonates, and phosphates. The borates or phosphates are preferred as buffers at the pH range of 7 to 9, where the oxydiacetaldehyde compositions exhibit the optimum activity. These buffers may be optimally used in concentrations of 0.1 to 1 percent (by weight) although higher concentrations may be employed if necessary.

Examples of usable organic alkalinating agents include the following types: (a) the alkali metal salts (preferably sodium or potassium) derived from the aliphatic or aromatic carboxylic acids, such as formates, acetates, propionates oxalates, malonates, citrates, nitrilotriacetate (NTA), ethylenediaminetetraacetate (EDTA), benzoate, salicylate, etc.; and, (b) the tertiary amines, such as trimethylamine, triethylamine, triethanolamine, etc., and (c) pyridine and the alkyl-substituted pyridines.

Compounds that are known to destroy the aldehyde functional group, such as the sulfites, bisulfites, and metabisulfites, as well as the primary and secondary amines, should not be used as alkalinating agents at a concentration of more than 0.2% by weight. The term "compatible alkalinating agent" as used herein is intended to include alkalinating agents, except for compounds which destroy the aldehyde functional group, and except for primary and secondary amines which are included only at concentrations of not more than 0.2% by weight.

5. Synergism between carboxylates and oxydiacetaldehyde: The carboxylates are useful not only for the purpose of raising the pH, but also as synergists. Although none of the carboxylates tested are active by themselves against bacterial spores at the concentration used (about 1%), the combination of oxydiacetaldehyde and carboxylates results in a number of synergistic, sporicidal compositions (see Table 5). The synergism is also evident in triple combinations of oxydiacetaldehyde, carboxylate (e.g., sodium acetate) and alcohol (e.g., isopropanol or ethanol) as shown in Table 5.

Although in most cases, the addition of a carboxylate to an oxydiacetaldehyde solution results in a slight decrease in the activity against vegetative bacteria, an exception is found in oxalate, which drastically reduces the concentrations of oxydiacetaldehyde required to kill *Staphylococcus aureus* and *Pseudomonas aeruginosa* respectively (see Table 5).

6. Effects of pH and temperature on the bactericidal activity of oxydiacetaldehyde: Oxydiacetaldehyde solutions kill vegetative bacteria over a wide pH range from 4 to 9 at room temperature, as shown by the data in Table 6. However, the sporicidal activity of oxydiacetaldehyde is more dependent on the pH. Significant kill-rates against bacterial spores were observed over the pH ranges from 7 to 9 at room temperature, and from 4 to 9 at temperatures above 30° C. (see Table 7). Furthermore, the compositions of this invention may be used in conjunction with ultrasonic energy for enhanced effect in the manner taught by Sierra U.S. Pat. No. 3,697,222 and Boucher U.S. Pat. No. 3,708,263.

7. Surfactants: Surfactants of any of the 4 types (nonionic, cationic, anionic and amphoteric) may be added to oxydiacetaldehyde solutions if so desired. For detergency, the concentration of surfactants may be optimally in the range from 0.1 to about 3% (by weight). The surfactants that have been tested thus far (cetylpyridinium chloride, Ethoquad C/25, sodium lauryl sulfate, Tergitol 15-S-12, Standapol ES-2, Uniterge-SK-2, at 0.25% respectively) all seem to have no significant effect one way or the other on the activity against bacterial spores which are suspended in water. While some surfactants seem to enhance the activity (e.g., by a factor of 2) against vegetative bacteria none of them has any adverse effect (See Table 8).

8. Another antimicrobial agent: If desired the oxydiacetaldehyde formulations of the present invention may have another antimicrobial agent incorporated therein, such as: (a) a monoaldehyde, e.g., formaldehyde, acetaldehyde, proprionaldehyde, butyraldehyde, (b) a $C_{2-6}$ saturated $\alpha,\omega$-dialdehyde, e.g., glyoxal, malonaldehyde, succinaldehyde, adipaldehyde and preferably, glutaraldehyde, (c) phenol, cresols or other disinfectants in the class of phenols, (d) quaternary ammonium compounds. The presence of any of the above is not essential to this invention, but rather optional.

9. Colorant: A colorant which may or may not indicate the solution pH by color may be added to the oxydiacetaldehyde solutions of the present invention. Such materials are typified by FD&C Green No. 8, FD&C Blue No. 1, FD&C Yellow No. 5, phenol red, rosolic acid, cresol red, etc. Such materials may optimally be used at about 0.0001%.

10. Corrosion Inhibitor: A corrosion inhibitor such as sodium nitrite or sodium nitrate may be added, if desired. These materials may optimally be used in the range of 0.01 to 0.1% by weight.

11. Aldehyde Stabilizer: An aldehyde stabilizer such as sodium formaldehyde sulfoxylate or the formaldehyde/sodium bisulfite adduct may be added. Such materials may optimally be used at 0.1 to 1% by weight.

12. Odorant: An odorant such as peppermint oil, mint, oil of wintergreen, pine oil, etc. may be used, if desired, especially where the oxydiacetaldehyde solution is to be used for disinfecting purposes. Such materials may optimally be used at about 0.01 to 0.1% by weight.

13. Aerosols: The oxydiacetaldehyde compositions may be used in aerosol form with an aerosol propellant, such as the Freons, which materials may be used for the purpose of propelling the oxydiacetaldehyde solution out of an aerosol container.

Advantages of the Invention

The oxydiacetaldehyde compositions of this invention do have advantages over alkalinated aqueous glutaraldehyde solutions in the following respects:

1. Oxydiacetaldehyde in solution has lower vapor pressure, and is nonvolatile and therefore does not produce vapor that is irritating to the human eye, whereas glutaraldehyde is volatile and can cause eye-irritation through vaporization under certain conditions if care is not taken in its use.

2. Oxydiacetaldehyde has a very slight and not unpleasant odor, whereas glutaraldehyde has a somewhat pronounced odor which has caused occasional complaints by users.

3. The compositions of the present invention, when activated with an alkalinating agent so as to be either neutral or on the basic side, age without leaving any precipitate in the container in which it is kept or on the objects treated therewith, whereas glutaraldehyde solutions, which have been "activated" with an alkalinating agent to a neutral pH or above, do leave a precipitate on aging and thus could leave an insoluble residue on treated objects.

Biological Test Procedures

The various tables to be presented hereinafter show the microbiological results obtained by the use of various compositions within the scope of the present invention. The microbiological evaluation thus presented is based on (a) the Minimum Killing Concentration Test of each composition against *Staphylococcus aureus* ATCC 6538 and *Pseudomonas aeruginosa* ATCC 15442 respectively, determined at 25° C. with a 10 minutes exposure time, (b) the A.O.A.C. Use-Dilution Test determined at 20° C. and (c) the Spore Rate of Kill Test. Tests (a) and (c) are described in detail below.

The Procedure of the Minimum Killing Concentration Test

The Minimum Killing Concentration Test is used to determine the minimum concentration of a disinfectant that is bactericidal in 10 minutes at 25° C. The materials used in this test are the following:
*Staphylococcus aureus*, ATCC 6538,
*Pseudomonas aeruginosa*, ATCC 15442,
Letheen Broth, and a
Transfer Loop, 4 mm in diameter
The Test Organisms used are prepared as follows:

1. Maintain stock cultures on nutrient agar slants by monthy transfers. Incubate new stock transfer 1–2 days at 37° C.; store at 2°–5°.

2. From stock culture inoculate tube of nutrient broth and make at least 4 consecutive daily transfers ($\leq 30$) in nutrient broth, incubating at 37°, before using culture for testing (1 daily transfer may be missed).

3. Use 22–26 hour culture of organism grown in nutrient broth at 37° in the test.

4. Aspirate *Staphylococcus aureus* cultures before use. Decant *Pseudomonas aeruginosa* cultures to remove the pellicle before use.

The Samples and Control used are prepared as follows:

1. Samples are prepared by adding 5 ml of each dilution to be tested to $25 \times 150$ mm. test tubes (medication tube). Dilutions are generally made as either 2-fold or 5-fold dilutions.

The Test Method used is as follows:

1. Place test samples into a 25° C. water bath and allow to come to temperature for at least 5 minutes.

2. Add 0.5 ml. test culture to each of the dilutions at 30 second intervals.

3. Agitate tubes by use of a vortex.

4. After allowing for an exposure time of 10 minutes, transfer a loopful from each medication tube to subculture tubes of Letheen broth.

5. Set positive viability controls of one loopful of organism per tube of Letheen broth. Static controls of one loopful of organism plus one loopful of disinfectant at the highest concentration tested should also be run. 6. Incubate Letheen broth tubes for 48 hours at 37° C. and read results.

The Calculations used to determine the results are as follows:

The minimum killing concentration is defined as the lowest concentration of a disinfectant which will kill *Pseudomonas aeruginosa* and *Staphylococcus aureus* in 10 minutes at 25° C., and is determined by dividing the original concentration tested by the highest dilution that was able to kill the test organism.

Example:

$$\frac{\text{Disinfectant Concentration}}{\text{Dilution factor}} = MKC$$

Disinfectant concentration = 2.0%
Effective dilution = 4×

$$MKC = \frac{2.0\%}{4} = 0.5\%$$

The Procedure of the Spore Rate of Kill Test

Nine ml. of the sporicidal solution to be tested are placed in a test tube which is half immersed in a water bath maintained at a constant temperature of 25° C. for a few minutes, followed by the addition of 1 ml. of a spore suspension containing approximately $10^7$ spores per ml. The spores used are of the species *Bacillus subtilis*, prepared according to the A.O.A.C. (the Association of Official Analytical Chemists) Sporicidal Test Procedure. The resultant mixture is briefly stirred on a vortex mixer, and the test tube is reimmersed in the water bath after 0.1 ml. of the mixture is withdrawn to be processed according to the following procedure.

Immediately after the spores are exposed to the sporicidal solution (at time zero), and then at 30 minute intervals, 0.1 ml. aliquots are withdrawn from the test tube and serial-diluted (by a factor ranging from 10 to $10^4$ depending on the number of viable spores present). One ml. of the resultant dilution is added along with 30 ml. of sterilized distilled water to a Millipore filter and filtered by suction through a 0.45 micron (pore size) membrane, which is then rinsed with 30 ml. of sterilized distilled water and placed on a nutrient agar petri plate. The latter is incubated at 37° C. for 48 hours and then stained with Crystal Violet. The number of bacterial colonies observed on the petri plate multiplied by the dilution factor gives the viable (or surviving) spore counts at a given time of exposure, S. The latter divided by the number of viable spores observed at time zero, namely $S/S_0$, gives the fractions of surviving spores, which are plotted on a semi-log graph paper against the exposure time to give the survivor-time curves.

Each survivor-time curve may be represented by two activity parameters, namely, the D-value and the $T_4$-value. The D-value is defined as the time required to reduced the viable spore popluation by a factor of 0.1 on the straight line portion of the curve. The $T_4$-value is defined as the time required to reduce the viable spore population by a factor of $10^{-4}$ from time zero.

The Specific Examples

Examples 1–61, exemplifying a great many different oxydiacetaldehyde (ODAA)—containing solution formulations within the scope of the present invention and also exemplifying some of the same formulations under different use conditions of application, appear in Tables 1–8 which follow. The formulations of each of the examples shown therein were prepared by simple admixture of all ingredients specified in each example. Unless specifically indicated to the contrary, all percentages of the various ingredients referred to are in terms of percentage by weight, and unless indicated to the contrary the solvent is water. Where sodium acetate or other sodium salts are reported as an ingredient if the pH is on the acid side the material will actually be present as the acid rather than the sodium salt.

Table 1 contains Examples 1–9, and shows the effect of 9 different oxydiacetaldehyde (ODAA) compositions and their activity against vegetative bacteria as measured by the Minimum Killing Concentration Test and against bacterial spores as determined by the Spore Rate of Kill Test.

Examples 1–3 utilize an aqueous solution of oxydiacetaldehyde alone at varying compositions at a pH which is neutral or slightly on the alkaline side. Examples 4–6 show the effect of adding varying amounts of an alcohol while Examples 7–9 show the effects of adding sodium acetate (or acetic acid depending on the pH) at acidic pH's, at basic pH's and at a slightly elevated temperature. (Thus, Example 8 shows the effect of the use of a slightly elevated temperature in increasing sporicidal activity and Example 9 shows that higher pH conditions are more sporicidal than lower pH conditions.)

Table 1

Activities of Different Oxydiacetaldehyde (ODAA) Compositions Against Vegetative Bacteria and Bacterial Spores

| Example | COMPOSITION, PERCENT | | | CONDITIONS OF APPLICATION | | ACTIVITY AGAINST VEGETATIVE BACTERIA[a] | | Activity against *Bacillus subtilis* Spores[b] |
|---|---|---|---|---|---|---|---|---|
| | ODAA | Acetate | Isopropanol | pH | Temp., °C. | S. aureus | P. aeruginosa | |
| 1 | 0.2 | 0 | 0 | 7–8 | 25 | Yes | No | No |
| 2 | 0.4 | 0 | 0 | 7–8 | 25 | Yes | Yes | No |
| 3 | 3 | 0 | 0 | 8 | 25 | Yes | Yes | Yes |
| 4 | 0.1 | 0 | 10 | 8 | 25 | Yes | No | No |
| 5 | 0.2 | 0 | 10 | 8 | 25 | Yes | Yes | No |
| 6 | 3 | 0 | 10–70 | 8 | 25 | Yes | Yes | Yes |
| 7 | 3 | 1 | 0 | 3–4 | 25 | Yes | Yes | No |
| 8 | 3 | 1 | 0 | 3–4 | >30 | Yes | Yes | Yes |
| 9 | 3 | 1 | 0 | 7–9 | 25 | Yes | Yes | Yes |

[a]As measured by the Minimum Killing Concentration in ten minutes against *Staphylococcus aureus* ATCC 6538 and *Pseudomonas aeruginosa* ATCC 15442.
[b]As determined by the Spore Rate of Kill test with a $T_4$-value less than 10 hours, where $T_4$ is the time required to reduce the viable spore population by a factor of $10^{-4}$.

Table 2 contains Examples 10–14, and shows the effect of varying only the oxydiacetaldehyde concentrations, where the solutions used are otherwise the same, against vegetative bacteria according to the A.O.A.C. Use-Dilution test. As can be seen, the higher the percentage of oxydiacetaldehyde present, the more active the solution becomes.

Table 2

The Activities of Different Oxydiacetaldehyde (ODAA) Concentrations Against Vegetative Bacteria According to the A.O.A.C. Use-Dilution Test.

| | | No. of failures/No. tested | |
|---|---|---|---|
| Example | percent ODAA[a] | Staphylococcus aureus | Pseudomonas aeruginosa |
| 10 | 3 | 0/20 | 0/20 |
| 11 | 2 | 0/20 | 2/20 |
| 12 | 1 | 0/20 | 2/20 |
| 13 | 0.5 | 0/20 | 4/20 |
| 14 | 0.25 | 6/20 | 5/20 |

[a]All solutions commonly consist of 1.4% sodium acetate, 1% sodium phosphate buffer, at pH 8.0.

Table 3, containing Examples 15–19 shows the effect of varying the oxydiacetaldehyde concentration on the sporicidal activity according to the Spore Rate of Kill Test. The solutions were the same except for the concentration of oxydiacetaldehyde and sporicidal activity increased as concentration increased.

addition of certain alcohols leads to a synergistic effect which increases with the amount of said alcohol, ethanol had no such effect.

Table 3

The Effect of Different Oxydiacetaldehyde Concentrations on the Sporicidal Activity According to the Spore Rate of Kill Test Activity against *Bacillus subtilis* spores at 25°

| Example | ODAA conc.[a] percent | D-Value[b] minutes | T4-Value[c] hours |
|---|---|---|---|
| 15 | 4 | 21 | 1.86 |
| 16 | 3 | 27 | 2.36 |
| 17 | 2 | 38 | 3.18 |
| 18 | 1 | 42 | 4.10 |
| 19 | 0.5 | 174 | 12.9 |

[a]All the solutions commonly consist of 1.4% sodium acetate, 1% phosphate buffer, at pH 8, plus varying concentrations of oxydiacetaldehyde as indicated in the column under ODAA conc.
[b]The time required to reduce the viable spore population by a factor of 0.1 in the straight line portion of the survivor-time curve.
[c]The time required to reduce the viable spore population by a factor of $10^{-4}$ from time zero.

Table 4 contains Examples 20–27, and is designed to show the effect of various alcohols and of various concentrations of alcohol on the bactericidal activities of oxydiacetaldehyde solutions which otherwise are identical and contain 3% oxydiacetaldehyde, 1% sodium phosphate buffer at pH 8.0. As can be seen, while the Table 4

Effect of Alcohols on the Bactericidal Activities of Aqueous Oxydiacetaldehyde Solutions

| | | Activity Against *Bacillus subtilis* Spores by the Spore Rate of Kill Test | | Minimum Killing Concentration with 10 Minutes Exposure | |
|---|---|---|---|---|---|
| | | | | *Staphylococcus aureus* | *Pseudomonas aeruginosa* |
| Example | Percent Alcohol Added[a] | D-Value[b] | T4-Value[c] | % ODAA | % ODAA |
| 20 | None | 131 mins | 8 hrs | 0.188 | 0.375 |
| 21 | 10% Isopropanol | 131 mins | 5.5 hrs | 0.094 | 0.188 |
| 22 | 30% Isopropanol | 93 mins | 5.0 hrs | — | — |
| 23 | 50% Isopropanol | 11 mins | 1.4 hrs | — | — |
| 24 | 70% Isopropanol | 11 mins | 1.0 hrs | 0.188 | 0.375 |
| 25 | 10% Propylene glycol | 54 mins | 7 hrs | 0.094 | 0.125 |
| 26 | 30% Ethanol | 130 mins | 8 hrs | 0.75 | 0.75 |
| 27 | 30% Hexyleneglycol | 84 mins | 7 hrs | 0.375 | 0.75 |

[a]All solutions employed commonly contain 3% oxydiacetaldehyde, 1% sodium phosphate buffer, at pH 8.0.
[b]The time required to reduce the viable spore population by a factor of 0.1 in the straight line portion of the survivor-time curve.
[c]The time required to reduce the viable spore population by a factor of $10^{-4}$ from time zero.

Table 5 contains Examples 28–40, and shows the effect of various alkalinating agents such as sodium acetate, disodium phosphate and other materials, some of which appear to have synergistic effect.

Table 5

Effect of Various Alkalinating Agents and Synergistic Agents on the Bactericidal Activity of Oxydiacetaldehyde Solutions at 25° C.

| | | Activity Against *Bacillus subtilis* Spores by the Spore Rate of Kill Test | | Minimum Killing Concentration with 10 Minutes Exposure | |
|---|---|---|---|---|---|
| | | | | *Staphylococcus aureus* | *Pseudomonas aeruginosa* |
| Example | Percent Alkalinating Agents[a] | D-Value[d] | T4-Value[e] | % ODAA | % ODAA |
| 29 | 1% P | 135 mins | >8 hrs | 0.19 | 0.38 |
| 29 | 1% P, 1.4% A | 33 mins | 2.7 hrs | 0.75 | 1.5 |
| 30 | 1% P, 1.4% Sodium Benzoate | 33 mins | 2.9 hrs | 0.13 | 0.38 |
| 31 | 1% P, 1.0% Sodium Citrate | 60 mins | 6.5 hrs | 0.13 | 0.19 |
| 32 | 1% P, 1.4% Sodium Formate | 33 mins | 2.8 hrs | 0.19 | 0.75 |
| 33 | 1% P, 1.4% Sodium Oxalate | 65 mins | 6.0 hrs | 0.062 | 0.094 |
| 34 | 1% P, 1.4% Sodium Salicylate | 36 mins | 4.1 hrs | 0.38 | 0.38 |
| 35 | 1.4% A, 1% Sodium Bicarbonate | 36 mins | 2.3 hrs | 0.38 | 0.75 |
| 36 | 1.4% A, 3% Sodium Bisulfite | (inactive) | | 0.75 | 1.5 |
| 37 | 1.4% A, 1% Borax | 40 mins | 2.5 hrs | 0.38 | 0.38 |
| 38 | 1.4% A, 1% Triethanolamine | 38 mins | 2.3 hrs | 0.50 | 0.75 |
| 39 | 1.4% A, 1% P (30% isopropanol)[b] | 8 mins | 0.88 hrs | 0.062 | 0.75 |
| 40 | 1.4% A, 1% P (30% ethanol)[c] | 26 mins | 2.3 hrs | 0.38 | 0.38 |

[a]All solutions commonly contain 3% oxydiacetaldehyde, with the pH adjusted to 8 with sodium hydroxide or hydrochloric acid. A = Sodium Acetate. P = Disodium Phosate.
[b]The solvent is 30% isopropanol - 70% ethanol - 70% water (v/v).
[d]The time required to reduce the viable spore population by a factor of 0.1 in the stright line portion of the survivor-time curve.
[e]The time required to reduce the viable spore population by a factor of $10^{-4}$ from time zero.

Table 6, containing Examples 41–45, shows the effect of pH on the bactericidal activity of oxydiacetaldehyde solutions which differ only in the pH used. The particular solutions involved are aqueous solutions containing 3% oxydiacetaldehyde, 1.4% sodium acetate and 1% sodium phosphate buffer, at pH's ranging from 4 to 9.

Table 6

Effect of pH on the Bactericidal Activity of Oxydiacetaldehyde Solutions According to the A.O.A.C. Use-Dilution Test (at 20° C.)

| | | Number of failures/number tested | |
|---|---|---|---|
| | | *Staphylococcus aureus* | *Pseudomonas aeruginosa* |
| Example | pH[a] | | |
| 41 | 4 | 0/20 | 0/20 |
| 42 | 6 | 0/20 | 1/20 |
| 43 | 7 | 0/20 | 0/20 |
| 44 | 8 | 0/20 | 0/20 |

Table 6-continued
Effect of pH on the Bactericidal Activity
of Oxydiacetaldehyde Solutions According
to the A.O.A.C. Use-Dilution Test (at 20° C.)

| Example | pH[a] | Number of failures/number tested | |
|---|---|---|---|
| | | Staphylococcus aureus | Pseudomonas aeruginosa |
| 45 | 9 | 0/20 | 0/20 |

[a]All solutions commonly contain 3% ODAA, 1.4% sodium acetate, and 1% sodium phosphate buffer.

Table 7 contains Examples 46–55, and shows the effects of varying the pH and of varying the temperature on the activity of 3% oxydiacetaldehyde solutions containing 1.4% sodium acetate and 1% sodium phosphate buffer.

Table 7
Effects of pH and Temperature on the Activity
of Oxydiacetaldehyde Solutions Against
Bacillus subtilis Spores According to the
Spore Rate of Kill Test.

| Example | pH[a] | Temp (°C.) | D-Value[b] (minutes) | T₄-Value[c] (hours) |
|---|---|---|---|---|
| 46 | 3 | 25 | No activity | No Activity |
| 47 | 7 | 25 | 38 | 4.50 |
| 48 | 8 | 25 | 32 | 2.75 |
| 49 | 9 | 25 | 37 | 2.25 |
| 50 | 4 | 30 | 250 | >8.0 |
| 51 | 4 | 40 | 24 | 2.03 |
| 52 | 4 | 50 | 6 | 0.60 |
| 53 | 8 | 30 | 14 | 1.30 |
| 54 | 8 | 40 | 6 | 0.40 |
| 55 | 8 | 50 | 4 | 0.30 |

[a]All the solutions commonly contain 3% ODAA, 1.4% sodium acetate (in acid or salt form), and 1% sodium phosphate buffer, except that solutions at pH 3 and 4 have no sodium phosphate buffer.
[b]The time required to reduce the viable spore population by a factor of 0.1 in the straight line portion of the survivor-time curve.
[c]The time required to reduce the viable spore population by a factor of $10^{-4}$ from time zero.

Table 8 contains Examples 56–61, and shows the effect of various anionic, non-ionic, cationic and amphoteric surfactants on the bactericidal and sporicidal activity of 3% aqueous oxydiacetaldehyde solutions containing 1.4% sodium acetate and 1% disodium phosphate buffer at pH 8.

Table 8
Effect of Various Types of Surfactants on the Bactericidal
Activity of Oxydiacetaldehyde Solutions

| Example | Percent Surfactant & Charge Type[a] | Activity Against Bacillus Subtilis Spores | | Minimum Killing Concentration With 10 Minutes Exposure | |
|---|---|---|---|---|---|
| | | D-Value[b] | T₄-Value[c] | S. aureus % ODAA | P. aeruginosa % ODAA |
| 56 | 0.25% Standapol ES-2, anionic | 29 mins. | 2.4 hrs. | 0.093 | 0.38 |
| 57 | 0.25% Tergitol 15-S-12, nonionic | 29 mins. | 2.4 hrs. | 0.093 | 0.38 |
| 58 | 0.25% Uniterge SK-2, amphoteric | 28 mins. | 2.4 hrs. | 0.19 | 0.19 |
| 59 | 0.25% Ethoquad C/25, cationic | 25 mins. | 2.3 hrs. | 0.093 | 0.19 |
| 60 | 0.25% Cetylpyridinium chloride, cationic | 22 mins.[e] | 1.9 hrs.[e] | 0.023[e] | 0.046[e] |
| 61 | 0.25% Cetylpyridinium chloride, control[d] | ( No Activity ) | | 0.023[e] | 0.046[e] |

[a]All solutions except the control commonly contain 3% oxydiacetaldehyde, 1.4% Sodium acetate and 1% Disodium phosphate buffer, at pH 8.0.
[b]The time required to reduce the viable spore population by a factor of 0.1 in the straight line portion of the survivor-time curve.
[c]The time required to reduce the viable spore population by a factor of $10^{-4}$ from time zero.
[d]Without oxydiacetaldehyde.
[e]The bacteriostatic activity of cetylpyridinium chloride may be a contributing factor to the apparent activity.

What is claimed is:

1. A sporicidal composition containing an aqueous solution of 3% oxydiacetaldehyde, 1.4% sodium acetate and 1% phosphate buffer at pH 8.

2. A method for disinfecting medical and surgical instruments and household objects which comprises subjecting said objects to treatment with a composition comprising an oxydiacetaldehyde-containing solution, wherein the oxydiacetaldehyde is present in an amount effective for disinfection and wherein the solution is an aqueous solution or a water solution containing an organic solvent as a cosolvent.

3. The method of claim 2 wherein the oxydiacetaldehyde-containing solution also contains a compatible alkalinating agent.

4. The method of claim 2 wherein the oxydiacetaldehyde-containing solution is an aqueous solution containing at least 0.2% by weight of oxydiacetaldehyde and having a pH in the range 4–9.

5. The method of claim 4 wherein the oxydiacetaldehyde containing solution also contains an alkali metal carboxylate.

6. A method of sterilizing a contaminated object which comprises contacting said object with an aqueous solution of a sporicidally effective amount of oxydiacetaldehyde whereby destruction of spores, if present, is effected.

7. The method of claim 6 wherein the oxydiacetaldehyde containing solution also contains a compatible alkalinating agent.

8. The method of claim 7 wherein the oxydiacetaldehyde-containing solution also contains a surfactant.

9. The method of claim 17 wherein the oxydiacetaldehyde-containing solution also contains isopropanol or propylene glycol.

* * * * *